United States Patent (10) Patent No.: US 7,659,363 B2
Rubroeder et al. (45) Date of Patent: Feb. 9, 2010

(54) PROCESS FOR THE PREPARATION OF INSULIN OR AN INSULIN DERIVATIVE IN THE PRESENCE OF OXYGEN

(75) Inventors: Franz-Josef Rubroeder, Villmar (DE); Reinhold Keller, Bad Soden (DE); Heike Herbert, Gernsheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 333 days.

(21) Appl. No.: 11/537,790

(22) Filed: Oct. 2, 2006

(65) Prior Publication Data

US 2007/0106063 A1 May 10, 2007

Related U.S. Application Data

(63) Continuation of application No. PCT/EP2005/002843, filed on Mar. 17, 2005.

(30) Foreign Application Priority Data

Apr. 1, 2004 (DE) .................. 10 2004 015 965

(51) Int. Cl.
*A61K 38/00* (2006.01)
(52) U.S. Cl. .................. 530/303; 530/324; 530/344
(58) Field of Classification Search .......... None
See application file for complete search history.

(56) References Cited

U.S. PATENT DOCUMENTS 5,407,810 A * 4/1995 Builder et al. ............ 435/69.1
6,380,355 B1 * 4/2002 Rubroder et al. ............ 530/303

FOREIGN PATENT DOCUMENTS

EP 0668292 8/1995
WO WO 01/46453 6/2001

* cited by examiner

*Primary Examiner*—Robert Landsman
*Assistant Examiner*—Gyan Chandra
(74) *Attorney, Agent, or Firm*—Balaram Gupta

(57) ABSTRACT

The present invention comprises a process for preparing insulin or an insulin derivative with correctly linked cysteine bridges from a precursor of said insulin or insulin derivative, wherein said precursor is subjected to a folding process in the presence of cysteine or cysteine hydrochloride and a chaotropic auxiliary compound. The insulin or insulin derivative with correctly linked cysteine bridges is obtained by enzymic cleavage by means of trypsin or a trypsin-like enzyme and, where appropriate, additionally by means of carboxypeptidase B and subsequent purification on an adsorber resin, which process is carried out at varied pH and temperature ranges.

16 Claims, No Drawings

US 7,659,363 B2

PROCESS FOR THE PREPARATION OF INSULIN OR AN INSULIN DERIVATIVE IN THE PRESENCE OF OXYGEN

CROSS-REFERENCE TO RELATED APPLICATIONS

This application is a continuation of International Application No. PCT/EP2005/002843 filed on Mar. 17, 2005 which is incorporated herein by reference in its' entirety which also claims the benefit of priority of German Patent Application No. 10 2004 015 965.3 filed on Apr. 1, 2004.

FIELD OF THE INVENTION

The present invention is directed to an improved process for the preparation of human insulin and/or insulin derivatives with correctly linked cysteine bridges from an insulin precursor by enzymic cleavage wherein said precursor is subjected to a folding process in the presence of cysteine or cysteine hydrochloride and a chaotropic auxiliary compound.

BACKGROUND OF THE INVENTION

The present invention relates to an improved process for obtaining insulins or insulin derivatives with correctly linked cystine bridges in the presence of cysteine or cysteine hydrochloride and of a chaotropic auxiliary compound, with folding being carried out in a reaction mixture in which the volume-to-surface ratio is greater than 1 and/or the oxygen concentration is 1-15 mg/l.

Human insulin is a protein with two amino acid chains of a combined 51 amino acid residues. The two amino acid chains contain 6 cysteine residues, with two cysteine residues being linked to one another via a disulfide bridge. In biologically active human insulin, the A and B chains are linked to one another via two cystine bridges and a further cystine bridge is present in the A chain. Statistically, 15 disulfide bridge formations are possible in one human insulin molecule. Only one of these 15 possible formations occurs in biologically active human insulin. The following cysteine residues are linked to one another in human insulin:

A 6-A 11
A 7-B 7
A 20-B 19

The letters A and B represent the respective insulin amino acid chain, and the number indicates the position of the amino acid residue, which is counted from the amino end to the carboxyl end of the particular amino acid chain. Disulfide bridges may also form randomly between any two human insulin molecules, enabling a vast number of different disulfide bridges to be produced easily.

A known process for preparing human insulin is based on the use of human proinsulin. Human proinsulin is a protein with a linear amino acid chain of 86 amino acid residues, in which the B and A chains of human insulin are linked to one another via a C peptide bridge containing 35 amino acid residues. The disulfide bridges present in human insulin are formed via an intermediate, with the cysteine residues of human insulin having a sulfur protective group, for example an S-sulfonate group (—S—$SO_3^-$: see EP 0 037 255). Another known process is one for obtaining proinsulin with correctly linked cystine bridges (Biochemistry, 60, (1968), pages 622 to 629) that starts from proinsulin obtained from pig pancreas in which the cysteine residues are present as thiol residues (—SH). The term "correctly linked cystine bridges" means the disulfide bridges which occur in biologically active mammalian insulin.

Genetic engineering processes allow precursors of insulin or insulin derivatives, in particular human proinsulin or proinsulin whose amino acid sequence and/or amino acid chain length deviate from human insulin, to be prepared in microorganisms. The proinsulins produced by genetically altered *Escherichia coli* cells do not have any correctly linked cystine bridges. One process for obtaining human insulin by using *E. coli* (EP 0 055 945) is based on the following steps:

Fermentation of microorganisms—disruption of cells—isolation of fusion protein—cyanogen halide cleavage of fusion protein—isolation of cleavage product having the proinsulin sequence—protection of proinsulin cysteine residues by S-sulfonate groups—chromatographic purification of S-sulfonate—formation of correctly linked cystine bridges—desalting of proinsulin—chromatographic purification of proinsulin with correctly linked cystine bridges—concentration of proinsulin solution—chromatographic purification of concentrated proinsulin solution—enzymatic cleavage of proinsulin to obtain human insulin—chromatographic purification of obtained human insulin.

Disadvantages of this process are the number of steps and the losses during the purification steps, resulting in a low insulin yield. Due to the multi-stage process route, considerable losses must be accepted. From the isolated fusion protein stage via cyanogen halide cleavage, sulfitolysis and purification of proinsulin, losses of up to 40% of proinsulin can be expected (EP 0 055 945). Losses of a similar size may occur during the subsequent purification steps up to the final product.

Increased yields can be obtained in the genetically engineered production of human insulin or insulin derivatives, if the number of steps required can be reduced substantially.

U.S. Pat. No. 5,473,049 to Obermeier et. al. (EP 0 600 372 A1) and EP 0 668 292 A2 disclose a correspondingly improved process for obtaining insulin and insulin derivatives, which involves converting the insulin precursor or insulin derivative precursor, whose cystine bridges are not correctly linked, to an insulin precursor or insulin derivative precursor, which has correctly linked cystine bridges, in the presence of a mercaptan, for example cysteine, and of at least one chaotropic auxiliary compound, for example urea or guanidine hydrochloride. The disclosed process comprises first dissolving said proteins in aqueous solutions of a chaotropic auxiliary compound or of mixtures of various chaotropic auxiliary compounds at a very low concentration. The protein mixture is then mixed with an aqueous mercaptan solution.

SUMMARY OF THE INVENTION

The present invention comprises a process for preparing insulin or an insulin derivative with correctly linked cysteine bridges from a precursor of said insulin or insulin derivative, wherein said precursor is subjected to a folding process in the presence of cysteine or cysteine hydrochloride and a chaotropic auxiliary compound. The insulin or insulin derivative with correctly linked cysteine bridges is obtained by enzymic cleavage by means of trypsin or a trypsin-like enzyme and, where appropriate, additionally by means of carboxypeptidase B and subsequent purification on an adsorber resin, which process is carried out at varied pH and temperature ranges.

DETAILED DESCRIPTION OF THE INVENTION

It has been found that the yields of correctly folded precursors of insulin or insulin derivatives can be increased and the reaction times for the folding process can be reduced, not by dissolving the precursor by means of the chaotropic auxiliary compound in a first step, but rather by first introducing the mercaptan, namely cysteine or cysteine hydrochloride, into the aqueous suspension of the precursor and, only in a subsequent step, dissolving the precursor by introduction into an aqueous solution of the chaotropic auxiliary compound and finally causing said precursor to fold correctly by diluting the mixture to a preferred cysteine or cysteine hydrochloride concentration, introducing said mixture into an appropriate amount of water.

Accordingly, the present invention relates to a process for obtaining a precursor of insulins or insulin derivatives with correctly linked cystine bridges in the presence of cysteine or cysteine hydrochloride and of a chaotropic auxiliary compound, which process comprises performing sequentially the following steps:

(a) adding an amount of cysteine or cysteine hydrochloride to an aqueous suspension of the precursor of insulins or insulin derivatives, resulting in 1 to 15 SH radicals of said cysteine or cysteine hydrochloride per cysteine residue of said precursor, (b) introducing the cysteine- or cysteine hydrochloride-containing suspension of the precursor into a 4 to 9 molar solution of the chaotropic auxiliary compound at a pH of from approximately 8.0 to approximately 11.5 and a temperature of from approximately 15.0 to approximately 55.0° C., keeping the resulting mixture at this temperature for about 10 to 60 minutes, and (c) introducing said mixture at a pH of from approximately 8.0 to approximately 11.5 and a temperature of from approximately 5.0 to approximately 30° C. into an amount of water resulting in the concentration of said cysteine or cysteine hydrochloride in said mixture being diluted to from about 1.0 to 5.0 mM and that of said chaotropic auxiliary compound being diluted to from 0.2 to 1.0 M, the mixture in step (c) being gassed in a container so that the concentration of oxygen in the suspension is from 1.0 to 15.0 mg/l, wherein the volume-to-surface ratio of the mixture is greater than 1 m, in particular greater than 2 m, in particular greater than 3 m, and the concentration of oxygen in the mixture is preferably from 2 to 10 mg/l.

Preferably, the process is also a process wherein, in step (a), the amount of cysteine or cysteine hydrochloride corresponds to an amount resulting in from 1 to 6—SH radicals of said cysteine or cysteine hydrochloride per cysteine residue of the precursor, In step (b), the cysteine- or cysteine hydrochloride-containing suspension of the precursor is introduced into a 4 to 9 molar solution of the chaotropic auxiliary compound at a pH of from 8 to 11 and a temperature of from 30 to 45° C., the resulting mixture is kept at this temperature for 20 to 40 minutes, and, In step (c), said mixture is introduced at a pH of from 8 to 11 and a temperature of from 15 to 20° C. into an amount of water resulting in the concentration of said cysteine or cysteine hydrochloride in said mixture being diluted to from about 1.0 to 5.0 mM and in a concentration of said chaotropic auxiliary compound of from 0.2 to 1.0 M.

Chaotropic auxiliary compounds are compounds which break hydrogen bonds in aqueous solution, for example, ammonium sulfate, guanidine hydrochloride, ethylene carbonate, thiocyanate, dimethyl sulfoxide and urea.

The chaotropic auxiliary compound employed in the process of the present invention is preferably guanidine, guanidine hydrochloride or, particularly preferably, urea.

The concentration of the chaotropic auxiliary compound in step (b) of the process of the invention is preferably from 7.0 to 9.0 M, the temperature in step (b) is preferably 40° C. and the pH in step (b) is preferably from 10 to 11.

The pH in step (c) of the process of the invention is preferably from 10.0 to 11.0. Also in step (c), the amount of water into which the mixture is introduced is preferably chosen so as to result in the concentration of the cysteine or cysteine hydrochloride in the mixture being diluted to from 2.5 to 3.0 mM and in a concentration of the chaotropic auxiliary compound of 0.5 M.

Particular preference is given to the process of the invention, wherein the concentration of the chaotropic auxiliary compound in step (b) is about 8 M, the temperature in step (b) is about 40° C., the pH in step (b) is about 10.2, the pH in step (c) is about 10.6 and, in step (c), the amount of water results in the concentration of the cysteine or cysteine hydrochloride in the mixture being diluted to from about 2.5 to 3.0 mM and in a concentration of the chaotropic auxiliary compound of 0.5 M.

The product of the process of the present invention is a precursor of insulin or insulin derivatives, in particular a proinsulin, whose cysteine bridges are correctly linked.

Insulin derivatives are derivatives of naturally occurring insulins, namely human insulin (see SEQ ID NO 1=A chain of human insulin; see SEQ ID NO 2=B chain of human insulin, sequence listing) or animal insulins, which differ from the corresponding, but otherwise identical, naturally occurring insulin by substitution of at least one naturally occurring amino acid residue and/or addition of at least one amino acid residue and/or organic residue.

Finally, an insulin or insulin derivative with correctly linked cystine bridges may be prepared from the insulin precursor or insulin derivative precursor obtained with the aid of the process of the present invention by the process described in EP 0 600 372 A1 (or U.S. Pat. No. 5,473,049) or in EP 0 668 292 A2 by enzymatic cleavage by means of trypsin or a trypsin-like enzyme and, where appropriate, additionally by means of carboxypeptidase B and subsequent purification on an adsorber resin.

The insulin or insulin derivative preparable from the precursor can preferably be described by the formula I below.

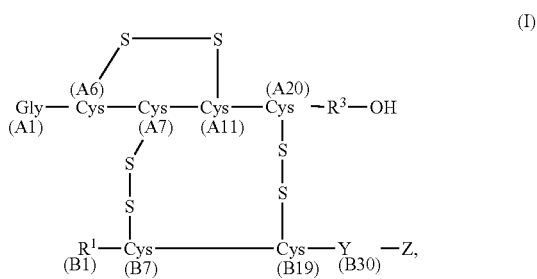

where

Y is a genetically encodable amino acid residue,

Z is an amino acid residue from the group consisting of His, Arg odor Lys, or is a peptide having 2 or 3 amino amino residues comprising the amino acid residue Arg or Lys at the carboxyl end of said peptide, or is a peptide having from 2 to 35 genetically encodable amino acids, comprising from 1 to 5 histidine residues, or is OH, $R^1$ is a phenylalanine residue (Phe) or a covalent bond, $R^3$ is a genetically encodable amino acid residue, with the residues A2-A20, not shown in order to simplify the formula I, corresponding to the amino acid sequence of the A chain of human insulin, animal insulin or an insulin derivative and the residues B2-B29, not shown in order to simplify the formula I, corresponding to the amino acid sequence of the B chain of human insulin, animal insulin or an insulin derivative.

The amino acid sequence of peptides and proteins is referred to starting from the N terminus of the amino acid chain. The information in parentheses in the formula I, for example A6, A20, B1, B7 or B19, corresponds to the positions of amino acid residues in the A and B chains of insulin.

The term "genetically encodable amino acid residue" is represented by the amino acids Gly, Ala, Ser, Thr, Val, Leu, Ile, Asp, Asn, Glu, Gin, Cys, Met, Arg, Lys, His, Tyr, Phe, Trp, Pro and selenocysteine.

The terms "residues A2-A20" and "residues B2-B29" of animal insulin mean, for example, the amino acid sequences of bovine, porcine or chicken insulin. The term "residues A2-A20" and "B2-B29" of insulin derivatives refers to the corresponding amino acid sequences of human insulin which are formed by replacing amino acids with other genetically encodable amino acids.

The A chain of human insulin, for example, has the following sequence (SEQ ID NO.: 1):

```
Gly Ile Val Glu Gln Cys Cys Thr Ser Ile Cys Ser

Leu Tyr Gln Leu Glu Asn Tyr Cys Asn.
```

The B chain of human insulin has the following sequence (SEQ ID NO.: 2):

```
Phe Val Asn Gln His Leu Cys Gly Ser His Leu Val

Glu Ala Leu Tyr Leu Val Cys Gly Glu Arg Gly Phe

Phe Tyr Thr Pro Lys Thr.
```

In this context, $R^3$ in the formula I is asparagine (Asn), $R^1$ is phenylalanine (Phe), Y is threonine (Thr) and Z is OH.

Accordingly, the process of the present invention is particularly suitable for obtaining a precursor of insulins or insulin derivatives which has the general formula II and whose cystine bridges (not shown in formula II) are correctly folded,

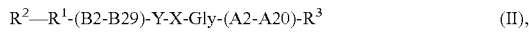

wherein $R^2$ is hydrogen, or is an amino acid residue from the group consisting of lysine (Lys) and arginine (Arg), or is a peptide having from 2 to 45 amino acid residues, comprising the amino acid residue lysine (Lys) or arginine (Arg) at the carboxyl end of said peptide, $R^1$ is a phenylalanine residue (Phe) or a covalent bond, (B2-B29) are the amino acid residues in positions B2 to B29 of the B chain of human insulin, animal insulin or of an insulin derivative which may have been modified in one or more of said positions, Y is a genetically encodable amino acid residue, X is an amino acid residue from the group consisting of lysine (Lys) and arginine (Arg), is a peptide having from 2 to 35 amino acid residues, comprising the amino acid residue lysine (Lys) or arginine (Arg) at the N terminus and at the carboxyl end of said peptide, or is a peptide having from 2 to 35 genetically encodable amino acids, comprising from 1 to 5 histidine residues, (A2-A20) are the amino acid residues in positions A2 to A20 of the B chain of human insulin, animal insulin or of an insulin derivative which may have been modified in one or more of said positions, and $R^3$ is a genetically encodable amino acid residue.

1. Preferably, in the formula II:

$R^2$ a) is hydrogen, or b) is a peptide having from 2 to 25 amino acid residues, comprising the amino acid residue arginine (Arg) at the carboxyl end of said peptide, $R^1$ is a phenylalanine residue (Phe), (B2-B29) are the amino acid residues in positions B2 to B29 of the B chain of human insulin, Y is an amino acid residue from the group consisting of alanine (Ala), threonine (Thr) and serine (Ser), X is the amino acid residue arginine (Arg) or a peptide having the amino acid sequence of the C chain of human insulin, (A2-A20) are the amino acid residues in positions A2 to A20 of the B chain of human insulin, and $R^3$ is an amino acid residue from the group consisting of asparagine (Asn), serine (Ser) and glycine (Gly).

The C chain of human insulin has the following sequence (SEQ ID NO.: 3):

```
Arg Arg Glu Ala Glu Asp Leu Gln Val Gly Gln Val

Glu Leu Gly Gly Gly Pro Gly Ala Gly Ser Leu Gln

Pro Leu Ala Leu Glu Gly Ser Leu Gln Lys Arg.
```

2. Preferably, in the formula II:

$R^2$ is hydrogen, or is a peptide having from 2 to 15 amino acid residues, whose carboxyl end comprises an arginine residue (Arg), $R^1$ is a phenylalanine residue (Phe), (B2-B29) are the amino acid residues in positions B2 to B29 of the B chain of human insulin, Y is a threonine residue (Thr), X is the amino acid residue arginine (Arg) or a peptide having from 2 to 35 amino acid residues, whose start and end comprise two basic amino acid residues, in particular arginine (Arg) and/or lysine (Lys), (A2-A20) are the amino acid residues in positions A2 to A20 of the B chain of human insulin, and $R^3$ is the amino acid residue asparagine (Asn) or glycine (Gly).

The residue Z of the insulin or insulin derivative of the formula I is usually part of the amino acid sequence of X of the precursor of the formula II and is formed by the activity of proteases such as trypsin, trypsin-like enzyme or carboxypeptidase B. The residue $R^3$ is the amino acid residue which is in position A21 of the insulin A chain. The residue Y is the amino acid residue which is in position B30 of the insulin B chain.

Trypsin or trypsin-like enzymes are proteases which cleave amino acid chains at an arginine or lysine residue.

Carboxypeptidase B is an exoprotease which removes basic amino acid residues, such as Arg or Lys, which are located at the carboxy terminus of amino acid chains (Kemmler et al., J. Biol. Chem. 246, pages 6786-6791).

It is possible, for example, to obtain an insulin or insulin derivative of the formula I with correctly linked cystine bridges from the precursor mentioned under 1, with Y, $R^1$, $R^2$, $R^3$, A2-A20 and B2-B29 being defined as under 1 and Z being an arginine residue (Arg), a peptide residue Arg-Arg, or —OH.

It is possible, for example, to obtain an insulin or insulin derivative of the formula I with correctly linked cystine bridges from the precursor mentioned under 2, with Y, $R^1$, $R^2$, $R^3$, A2-A20 and B2-B29 being defined as under 2 and Z being an arginine residue (Arg), a peptide residue Arg-Arg or Lys-Lys, or —OH.

The precursor of the formula II may be produced with a multiplicity of genetically engineered constructs in microorganisms (EP 0 489 780, EP 0 347 781, EP 0 453 969). Said genetically engineered constructs are expressed in microorganisms such as *Escherichia coli* or streptomycetes during fermentation. The proteins produced are stored inside the microorganisms (EP 0 489 780) or secreted into the fermentation solution.

It is possible to use for the process of the invention precursors of insulins or of insulin derivatives of the formula II, which precursors are, immediately after the cells have been disrupted, still contaminated with a multiplicity of proteins from the fermentation solution or from the microorganisms. However, the precursors of the formula II may also be used in prepurified form, for example after precipitation or chromatographic purification.

The following examples are provided to more specifically describe the process(es) of the present invention so as to enable one skilled in the art to better practice all the various aspects thereof. They are for illustrative purposes only however, and should not be construed as limiting the spirit and scope of the invention as defined and set forth by the claims that follow.

EXAMPLE 1 (COMPARATIVE EXAMPLE, PRIOR ART)

A fusion protein is produced by fermentation of genetically modified *Escherichia coli* cells (EP 0 489 780). This protein has the following amino acid sequence.

Proinsulin sequence 1 (Seq Id No. 4):

```
Ala Thr Thr Ser Thr Gly Asn Ser Ala Arg Phe Val

Asn Gln His Leu Cys Gly Ser His Leu Val Glu Ala

Leu Tyr Leu Val Cys Gly Glu Arg Gly Phe Phe Tyr

Thr Pro Lys Thr Arg Arg Glu Ala Glu Asp Leu Gln

Val Gly Gln Val Glu Leu Gly Gly Gly Pro Gly Ala

Gly Ser Leu Gln Pro Leu Ala Leu Glu Gly Ser Leu

Gln Lys Arg Gly Ile Val Glu Gln Cys Cys Thr Ser

Ile Cys Ser Leu Tyr Gln Leu Glu Asn Tyr Cys Asn
```

Proinsulin sequence 1 corresponds to the formula II, where
X is the C peptide of human insulin,
Y is Thr (B30),
$R^1$ is Phe (B1),
$R^2$ is a peptide having 11 amino acid residues,
$R^3$ is Gly (A21) and
A2-A20 is the amino acid sequence of the A chain of human insulin (amino acid residues 2 to 20) and B2-B29 is the amino acid sequence of the B chain of human insulin (amino acid residues 2 to 29).

The expressed fusion protein having the proinsulin sequence 1 accumulates in the *E. coli* cells, forming inclusion bodies. After completion of the fermentation, the cells are removed by centrifugation and disrupted by customary high pressure homogenization. The released fusion protein inclusion bodies are isolated by centrifugation.

The aqueous fusion protein suspension containing 40 kg of fusion protein (determined by freeze-drying of an aliquot), is admixed with 5 kg of cysteine hydrochloride hydrate.

The suspension (the proportion of the insulin-containing fusion protein is determined with the aid of high pressure liquid chromatography (HPLC) and is 50%) is dissolved with the proinsulin sequence 1 in 550 l of an 8 M urea solution at pH 10.2 and 40° C. The clear solution is stirred into 9000 l of water at a pH of 10.6 and a temperature of 16° C. After 4 hours with stirring, a content of 5 kg of proinsulin sequence I with correctly linked cystine bridges in the reaction mixture is determined with the aid of analytical HPLC, corresponding to 25% conversion.

The 9500 l solution is adjusted to pH 5.0 with 1N HCl and separated. The solution is then adjusted to pH 9 by adding 1 N sodium hydroxide solution. 10 g of trypsin are introduced into the solution. Approx. 2.2 kg of insulin precursor 2 are produced, as measured by HPLC.

Insulin 2 corresponds to the formula I, where
Y is Thr (B30),
Z is Arg-Arg,
$R^1$ is Phe (B1),
$R^3$ is Gly (A21) and
A2-A20 is the amino acid sequence of the A chain of human insulin (amino acid residues 2 to 20) and B2-B29 is the amino acid sequence of the B chain of human insulin (amino acid residues 2 to 29).

Insulin 2 consists of an A chain having the sequence

```
Gly Ile Val Glu Gln Cys Cys Thr Ser   (SEQ ID NO: 5)

Ile Cys Ser Leu Tyr Gln Leu Glu Asn

Tyr Cys Gly
``` and a B chain having the sequence

```
Phe Val Asn Gln His Leu Cys Gly Ser   (SEQ ID NO: 6)

His Leu Val Glu Ala Leu Tyr Leu Val

Cys Gly Glu Arg Gly Phe Phe Tyr Thr

Pro Lys Thr Arg Arg
``` which are linked to one another via correctly bound cystine bridges.

The solution is concentrated and purified by means of adsorber resin.

The eluate which contains insulin 2 may, after dilution with water and pH adjustment, immediately be purified further on a chromatography column.

EXAMPLE 2 (PROCESS OF THE PRESENT INVENTION)

A fusion protein having the amino acid sequence proinsulin sequence 1 (SEQ ID NO: 4) is produced by fermentation of genetically modified *Escherichia coli* cells (EP 0 489 780).

The expressed fusion protein having the proinsulin sequence 1 accumulates in the *E. coli* cells, forming inclusion bodies. After completion of the fermentation, the cells are removed by centrifugation and disrupted by customary high pressure homogenization. The released fusion protein inclusion bodies are isolated by centrifugation.

The aqueous fusion protein suspension containing 40 kg of fusion protein (determined by freeze-drying of an aliquot), is admixed with 5 kg of cysteine hydrochloride hydrate.

The suspension (the proportion of the insulin-containing fusion protein is determined with the aid of HPLC and is 50%) is dissolved with the proinsulin sequence 1 in 550 l of an 8 M urea solution at pH 10.2 and 40° C. The clear solution is stirred into 9000 l of water at a pH of 10.6 and a temperature of 15° C. This involves gassing the gas space of the container with air passing over the stirred mixture at a rate of 4 m$^3$/h during the entire reaction time. In the container which has a volume of 10 000 l and a diameter of 2000 mm and has two baffles above the cylindrical section, a three-step trapezoid stirrer with a stirring element 1100 mm in diameter and an electric power of 2 kW circulates the 9500 l of folding solution so as to ensure mixing of the contents with gas all the way to the bottom. The volume-to-surface ratio of the reaction mixture is 1:3.14. The oxygen content was maintained at 8 mg/l by stirring and gassing.

After 4 hours and completion of the folding reaction, a content of 10.0 kg of proinsulin sequence I with correctly linked cystine bridges in the reaction mixture is determined with the aid of analytical HPLC, corresponding to 50% conversion.

The 9500 l solution is adjusted to pH 5.0 with 1N HCl and separated. The solution is then adjusted to pH 9 by adding 1 N sodium hydroxide solution. 10 g of trypsin are introduced into the solution. 4.5 kg of insulin 2 are produced, as measured by HPLC.

The solution is concentrated and purified by means of adsorber resin.

The eluate which contains insulin 2 may, after dilution with water and pH adjustment, immediately be purified further on a chromatography column.

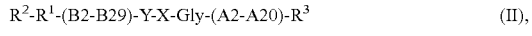

What is claimed is:

1. A process for the preparation of insulin or an insulin derivative with correctly-linked cysteine bridges from a precursor of said insulin or insulin derivative, wherein said precursor is subjected to a folding process in the presence of cysteine or cysteine hydrochloride and a chaotropic auxiliary compound, wherein said insulin or insulin derivative is obtained by enzymatic cleavage by means of trypsin or a trypsin-like enzyme and optionally, by means of carboxypeptidase B and subsequent purification on an adsorbant resin, which process comprises:

(a) adding an amount of cysteine or cysteine hydrochloride to an aqueous suspension of the precursor of insulin or insulin derivatives, resulting in 1 to 15 SH radicals of said cysteine or cysteine hydrochloride per cysteine residue of said precursor, (b) introducing the cysteine- or cysteine hydrochloride-containing suspension of the precursor into approximately a 4.0 to a 9.0 molar solution of the chaotropic auxiliary compound at a pH of from approximately 8 to approximately 11.5 and a temperature of from approximately 15 to approximately 55° C., keeping the resulting mixture at this temperature for about 10 to 60 minutes, and (c) introducing said mixture at a pH of from approximately 8.0 to approximately 11.5 and a temperature of from approximately 5.0 to approximately 30° C. into an amount of water resulting in the concentration of said cysteine or cysteine hydrochloride in said mixture being diluted to from about 1.0 to about 5.0 mM and that of said chaotropic auxiliary compound being diluted to from about 0.2 to 1.0 M, and the mixture in step (c) being gassed in a container so that the concentration of oxygen in the suspension is from about 1.0 to about 15.0 mg/l.

2. The process as claimed in claim 1, wherein the volume-to-surface ratio of the mixture in step (c) is greater than 1.

3. The process as claimed in claim 2, wherein the volume-to-surface ratio of the mixture is greater than 2.

4. The process as recited in claim 1 wherein the concentration of oxygen in the mixture is from about 2.0 to 10 mg/l.

5. The process as recited in claim 3 wherein the concentration of oxygen in the mixture is from 2 to 10 mg/l.

6. The process as recited in claim 1 wherein, in step (a), the amount of cysteine or cysteine hydrochloride corresponds to an amount resulting in from 1 to 6 SH radicals of said cysteine or cysteine hydrochloride per cysteine residue of the precursor, in step (b), the cysteine- or cysteine hydrochloride-containing suspension of the precursor is introduced into about a 4.0 to 9.0 molar solution of the chaotropic auxiliary compound at a pH of from about 8.0 to about 11.0 and a temperature of from about 30 to 45° C., the resulting mixture is kept at this temperature for 20 to 40 minutes, and, in step (c), said mixture is introduced at a pH of from about 8.0 to about 11.0 and a temperature of from about 15 to about 20° C. into an amount of water resulting in the concentration of said cysteine or cysteine hydrochloride in said mixture being diluted to from about 1.0 to about 5.0 mM and in a concentration of said chaotropic auxiliary compound of from about 0.2 to 1.0 M.

7. The process as recited in claim 6 wherein the chaotropic auxiliary compound is guanidine, guanidine hydrochloride or urea.

8. The process as recited in claim 7 wherein the concentration of the chaotropic auxiliary compound in step (b) is from 7.0 to 9 M.

9. The process as recited in 8 wherein the temperature in step (b) is about 40° C.

10. The process as recited in claim 9, wherein the pH in step (b) is from about 10 to 11.

11. The process as recited in 10, wherein the pH in step (c) is from about 10.0 to about 11.0.

12. The process as recited in claim 11, wherein the amount of water in step (c) results in the concentration of the cysteine or cysteine hydrochloride in the mixture being diluted to from about 2.5 to 3.0 mM and in a concentration of the chaotropic auxiliary compound of 0.5 M.

13. The process as recited in claim 12, wherein the concentration of the chaotropic auxiliary compound in step (b) is about 8 M, the temperature in step (b) is about 40° C., the pH in step (b) is about 10.2, the pH in step (c) is about 10.6 and, in step (c), the amount of water results in the concentration of the cysteine or cysteine hydrochloride in the mixture being diluted to from about 2.5 to about 3.0 mM and in a concentration of the chaotropic auxiliary compound of about 0.5 M.

14. The process as recited in claim 13, wherein the precursor of the insulin or insulin derivatives has the sequence of the general formula II $$R^2\text{-}R^1\text{-}(B2\text{-}B29)\text{-}Y\text{-}X\text{-}Gly\text{-}(A2\text{-}A20)\text{-}R^3 \qquad (II),$$

wherein:
$R^2$ is hydrogen, or
is an amino acid residue from the group consisting of lysine (Lys) and arginine (Arg), or
is a peptide having from 2 to 45 amino acid residues, comprising the amino acid residue lysine (Lys) or arginine (Arg) at the carboxyl end of said peptide, $R^1$ is a phenylalanine residue (Phe) or a covalent bond, (B2-B29) are the amino acid residues in positions B2 to B29 of the B chain of human insulin, animal insulin or of an insulin derivative which may have been modified in one or more of said positions, Y is a genetically encodable amino acid residue, X is an amino acid residue from the group consisting of histine (His), lysine (Lys) and arginine (Arg), or
is a peptide having from 2 to 35 amino acid residues, comprising the amino acid residue lysine (Lys) or arginine (Arg) at the N terminus and at the carboxyl end of said peptide, or
is a peptide having from 2 to 35 genetically encodable amino acids, comprising from 1 to 5 histidine residues, (A2-A20) are the amino acid residues in positions A2 to A20 of the B chain of human insulin, animal insulin or of an insulin derivative which may have been modified in one or more of said positions, and $R^3$ is a genetically encodable amino acid residue.

15. The process as recited in claim 14 wherein in formula II,
$R^2$ is hydrogen, or
is a peptide having from 2 to 25 amino acid residues, comprising the amino acid residue arginine (Arg) at the carboxyl end of said peptide, $R^1$ is a phenylalanine residue (Phe), (B2-B29) are the amino acid residues in positions B2 to B29 of the B chain of human insulin, Y is an amino acid residue from the group consisting of alanine (Ala), threonine (Thr) and serine (Ser), X is the amino acid residue arginine (Arg) or a peptide having the amino acid sequence of the C chain of human insulin, (A2-A20) are the amino acid residues in positions A2 to A20 of the B chain of human insulin, and $R^3$ is an amino acid residue from the group consisting of asparagine (Asn), serine (Ser) and glycine (Gly).

16. The process as recited in claim 13, wherein, in the formula II,
$R^2$ a) is hydrogen, or
b) is a peptide having from 2 to 15 amino acid residues, whose carboxyl end comprises an arginine residue (Arg), $R^1$ is a phenylalanine residue (Phe), (B2-B29) are the amino acid residues in positions B2 to B29 of the B chain of human insulin, Y is a threonine residue (Thr), X is the amino acid residue arginine (Arg) or a peptide having from 2 to 35 amino acid residues, whose start and end comprise two basic amino acid residues, in particular arginine (Arg) and/or lysine (Lys), (A2-A20) are the amino acid residues in positions A2 to A20 of the B chain of human insulin, and $R^3$ is the amino acid residue asparagine (Asn) or glycine (Gly).

SEQUENCE LISTING

```
<160> NUMBER OF SEQ ID NOS: 6

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 35
<212> TYPE: PRT
<213> ORGANISM: Homo sapiens

<400> SEQUENCE: 3

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
```

-continued

```
<210> SEQ ID NO 4
<211> LENGTH: 96
<212> TYPE: PRT
<213> ORGANISM: Homo sapiens

<400> SEQUENCE: 4

Ala Thr Thr Ser Thr Gly Asn Ser Ala Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Pro Lys Thr Arg Arg Glu Ala Glu Asp Leu Gln
        35                  40                  45

Val Gly Gln Val Glu Leu Gly Gly Pro Gly Ala Gly Ser Leu Gln
    50                  55                  60

Pro Leu Ala Leu Glu Gly Ser Leu Gln Lys Arg Gly Ile Val Glu Gln
65                  70                  75                  80

Cys Cys Thr Ser Ile Cys Ser Leu Tyr Gln Leu Glu Asn Tyr Cys Asn
                85                  90                  95

<210> SEQ ID NO 5
<211> LENGTH: 21
<212> TYPE: PRT
<213> ORGANISM: Homo sapiens

<400> SEQUENCE: 5

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 6
<211> LENGTH: 32
<212> TYPE: PRT
<213> ORGANISM: Homo sapiens

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```